(12) United States Patent
Zeder

(10) Patent No.: US 11,385,170 B2
(45) Date of Patent: Jul. 12, 2022

(54) PLATE WITH WELLS FOR CHEMICAL OR BIOLOGICAL REACTIONS, AND METHOD FOR MULTIPLE IMAGING OF SUCH A PLATE BY MEANS OF AN IMAGING SYSTEM

(71) Applicant: Roche Molecular Systems, Inc., Pleasanton, CA (US)

(72) Inventor: Michael Zeder, Buchrain (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 158 days.

(21) Appl. No.: 15/671,334

(22) Filed: Aug. 8, 2017

(65) Prior Publication Data
US 2018/0045641 A1 Feb. 15, 2018

(30) Foreign Application Priority Data
Aug. 10, 2016 (EP) .................................... 16183569

(51) Int. Cl.
*G01N 21/25* (2006.01)
*G01N 35/00* (2006.01)
(Continued)

(52) U.S. Cl.
CPC ........ *G01N 21/253* (2013.01); *B01J 19/0046* (2013.01); *B01L 3/5027* (2013.01); *B01L 3/5085* (2013.01); *C12Q 1/6834* (2013.01); *G01N 35/00732* (2013.01); *G01N 35/028* (2013.01); *B01L 2200/025* (2013.01); *B01L 2300/021* (2013.01); *B01L 2300/0829* (2013.01); *B01L 2300/0851* (2013.01); *G01N 2035/00772* (2013.01); *G01N 2035/0493* (2013.01)

(58) Field of Classification Search
CPC . B01J 19/0046; G01N 21/253; G01N 35/028; G01N 35/00732; G01N 2035/00772; G01N 2035/0493; C12Q 1/6834; B01L 3/5085; B01L 3/5027; B01L 2300/0851; B01L 2300/0829; B01L 2300/021; B01L 2200/025
See application file for complete search history.

(56) References Cited

U.S. PATENT DOCUMENTS 8,367,016 B2 2/2013 Quan et al.
8,808,647 B2 * 8/2014 Cherubini et al. .. B01L 3/50851
422/553

(Continued)

OTHER PUBLICATIONS

Search Report for EP16183569 (dated Feb. 23, 2017).

*Primary Examiner* — Gautam Prakash
(74) *Attorney, Agent, or Firm* — Maneesh Gupta

(57) ABSTRACT

The present disclosure provides a plate comprising an array of wells for chemical or biological reactions, wherein each of the wells comprises a reaction chamber with at least one opening on a surface of the plate. The array of wells consist of a plurality of adjacent blocks of wells, wherein each block of wells consists of a plurality of adjacent rows of wells, and wherein at least one void is provided in each block of wells in between the rows of wells. Here, the void is particularly part of the surface of the plate and lacks a well opening. Furthermore, a method for multiple imaging of such a plate by means of an imaging system is provided with the present disclosure.

16 Claims, 5 Drawing Sheets

(51) Int. Cl.
  *B01J 19/00* (2006.01)
  *B01L 3/00* (2006.01)
  *C12Q 1/6834* (2018.01)
  *G01N 35/02* (2006.01)
  *G01N 35/04* (2006.01)

(56) References Cited

U.S. PATENT DOCUMENTS

| | | |
|---|---|---|
| 2003/0152256 A1 | 8/2003 | Kira et al. |
| 2012/0242825 A1 | 9/2012 | Quan et al. |
| 2013/0273645 A1* | 10/2013 | Waga ................ B01L 3/545 |
| | | 435/287.2 |
| 2013/0344473 A1 | 12/2013 | Deutsch et al. |
| 2016/0032230 A1 | 2/2016 | Deutsch et al. |

* cited by examiner

PLATE WITH WELLS FOR CHEMICAL OR BIOLOGICAL REACTIONS, AND METHOD FOR MULTIPLE IMAGING OF SUCH A PLATE BY MEANS OF AN IMAGING SYSTEM

CROSS-REFERENCE TO RELATED APPLICATION

The present application claims the benefit of priority under 35 U.S.C. § 119(a) of EP16183569.9, filed Aug. 10, 2016. Reference is also made to EP16002058.2, filed Sep. 23, 2016; EP16002057.4, filed Sep. 23, 2016; and EP16191425.4, filed Sep. 29, 2016; and EP16400045.7, EP16191771.1, EP16400044.0; EP16191811.5, each filed September 30. The disclosures of each of these applications are incorporated herein by reference in their entireties.

BACKGROUND

In general, the present disclosure relates to a plate comprising wells for chemical or biological reactions, such as a multiwell plate in the form of a microwell plate, microplate, picowell plate or the like, which all can generally also be referred to as well plate, and further to a method for multiple imaging of such a well plate, for the study of the chemical or biological reactions occurring in the wells. In particular, the present disclosure is directed to an improved well plate, which can be used as disposable item, and an improved method for measuring the outcomes of the reactions inside the wells of the well plate.

For many biological, biochemical, diagnostic or therapeutic applications, it is necessary to accurately determine the amount or concentration of a certain substance or compound in a sample, such as in the course of a polymerase chain reaction (FOR), for example a real-time PCR or a digital polymerase chain reaction (dPCR), or the like. Most of these applications, usually in the form of chemical, biochemical and/or biological assays, are directed to the immobilization of biological materials such as polypeptides and nucleic acids, cells or tissues within reaction chambers and the performance of one or more reactions with the immobilized material, followed by a quantitative and/or qualitative analytical process, such as luminescence test measurements. Here, recent developments have contributed to the efficiency of these analytical processes, for example by means of computer control for automatic focusing and microscope stage positioning of the respective reaction chambers, which have been developed to facilitate the repeated imaging of biological samples inside these chambers.

For the purpose of analyzing multiple biological samples, well plates, or more particularly multiwell plates have been and are still widely used as standard tools in analytical research and clinical diagnostic testing laboratories, which multiwell plates are commonly used in the form of a disposable for one-time use. In more detail, a multiwell plate simply constitutes a preferably flat plate comprising a multitude of reaction chambers in the form of wells or cavities which are used as test tubes for the biological samples, wherein the multiwell plate can be made from any suitable kind of available material, such as glass, plastics, quartz and silicon and typically provides 6, 24, 96, 384, 1536 or even more sample wells which are usually arranged in a 2:3 rectangular matrix. The standardization of the formats of multiwell plates, in particular in view of the arrangement of its wells, provides a significant advantage since the standardization allows the use of standardized laboratory devices such as robotic handling devices, automated sample handling devices, sample dispensers, as well as multiwell plate readers or reaction observation devices. With special regard to readers or observation devices, optical detection is the most commonly used method for measuring reactions, particularly with regard to arrays of wells representing a multitude of different reactions.

However, due to the possibility of using a multiwell plate with a more or less unlimited number of sample wells, it becomes more and more cumbersome to correlate the multitude of observed wells to the reaction taking place inside each well. Here, one method of implementing such individual correlations is the arrangement of the wells in a predetermined order, for example in one long single row, and finding a specific desired well by simple counting. Another method of identifying the desired well within the multitude of wells is by the use of particular markers such as fiducial points, also referred to as fiducial markers, fiducial marks or simply as fiducials, which make it possible to correlate each single well to a combination of one fiducial assigned to a row of wells and one fiducial assigned to a column of wells inside an array of wells. As an example for the use of such fiducial markers. US2016032230A1 describes a multiwell plate with an array of wells, wherein picowells are provided on the bottom of the wells, and wherein it is described with reference to the known prior art as well as to an embodiment as shown in attached FIG. 3 that fiducial markers are used to identify each single well. Here, the shown multiwell plate 9 comprises 96 wells and consists of 8 rows and 12 columns of wells 91, wherein an alphabetic character with the reference number 92, such as A, B, C, etc., is assigned to each row, and wherein a number with the reference number 93, such as 1, 2, 3, etc., is assigned to each column of the multitude of wells 91, in order to clearly identify each well 91. For example, the well in the upper left corner of the multiwell plate 9 comprises the assigned fiducial markers "A" and "1," i.e., "A1" in combination.

In the above described example of known prior art, the cross section of each well 91 is of a circular shape. However, in recent years, it became clear that a hexagonal shape, at least at the level of the surface of the multiwell plate, would improve the density of distribution of wells on a multiwell plate, see attached FIG. 4. Also, as already described, the number of wells of a commonly known multiwell plate already increased to more than 96 in order to be able to carry out more and more analytical processes parallel to each other, with a multitude of samples. Now, in order to be able to automatically grasp the array of wells with such a high number of wells, an imaging device such as a camera or the like can be used, which camera comprises a so-called field of view 94, see also FIG. 4, which field of view, or also referred to as FOV or imaging area, usually constitutes an angular size of a view cone of the camera and is illustrated as a rectangular square marked by a dashed line in FIG. 4.

For imaging parts or areas of the well array that exceed the camera's FOV by size, i.e. the wells that are not fully arranged inside the rectangular square in FIG. 4, it is a possibility to acquire multiple images, spatially shifted, in order to be able to piecewise image the full array area. Here, however, it is crucial to be able to identify how the multiple images taken by the camera are related to each other, i.e. are to be put together, in order not to miss any wells of the multiwell plate, or not to count wells twice and, thus, tamper with the measuring results. Basically, each well on the array of wells has to be directly identifiable, which, again, requires an identification of each image representing a particular FOV of the camera. For this purpose, fiducial markers 95 are usually used for orientation, in order to be able to identify the wells covered by the respective FOV 94, see FIG. 4. The used fiducial markers are symbolized in FIG. 4 by the expressions "F1," "F2" and "F3," and they can be any machine readable structure positioned outside the well array. At least one fiducial marker has to be present within any image, i.e. within any FOV, in order to serve as a reference for all wells in this image. As an example, U.S. Pat. No. 8,367,016 B2 discloses complicated structures of a so-called microfluidic device, with different depths and heights, wherein blank spaces between wells or around wells are necessary for the placement and discrimination of the respective fiducials markers.

Accordingly, the disadvantage of fiducial markers implemented as additional physical structures is that they require additional process steps when manufacturing the respective disposable well plate, rendering the well plate more expensive and complex. In addition thereto, the fiducial markers use up valuable physical space that is lost for the provision of additional wells on the actual well plate. Accordingly, reserving space on the plate, which implicitly also requires reserving valuable space in the camera's FOV, significantly reduces the usability and the exploitation of the well plate. Also, the fiducial markers can actually interfere with a functionality of the well plate, such as microfluidic properties in case of a microfluidic plate. Moreover, including the fiducial markers which are positioned outside the area of interest, i.e. the area covering the actual wells to be captured, into the FOV of an imaging device require the FOV to be significantly larger than the area of interest, or which require the area of interest to be substantially smaller than the FOV, which either way leads to a less efficient imaging method of the well plate.

Thus, there is a significant demand for an improved well plate as well as for an improved method of multiple imaging of such a plate, which avoid the above discussed disadvantages.

SUMMARY

The disclosure provides a multi-well plate comprising a top surface including an array of M×N positions, wherein M and N are integers greater than zero and each position is selected from (i) a well opening defining a reaction chamber for a chemical or biological reaction, or (ii) a closed space, wherein the array comprises two or more blocks, each block comprising a group of positions numbering between one and a number fewer than the total number of positions in the array, and each block comprises a block-identifying pattern of positions including at least one closed space position. The block-identifying pattern of positions can include at least two closed space positions, e.g., the at least two closed space positions are located in a row of positions comprising a plurality of well openings and the at least two closed space positions; the at least two closed space positions are adjacent to one another in the row; the at least two closed space positions are not adjacent to one another and separated in the row by at least one well opening; the at least two closed space positions are separated in the row by at least two well openings; and/or the at least two closed space positions are located in two or more rows of positions.

In this embodiment, the array can include (i) a first row of positions comprising a first closed space position and two or more well openings, and (ii) a second row of positions comprising a second closed space position and two or more well openings. For example, the first and second closed space positions are adjacent to one another in the block. Alternatively, the first and second closed space positions are not adjacent to one another in the block and separated in the block by at least one well opening. Still further, the first and second closed space positions can be separated in the block by at least one row of positions.

Moreover, the plate provided herein can include an array boundary and the array further comprises internal and external positions, the external positions being adjacent to the array boundary and the internal positions being removed from the array boundary. The at least one closed space position can occupy an internal position.

Still further, the block can correspond to a field of view of an imaging device.

Yet another embodiment provided herein is a plate (1; 2) comprising an array of wells (11; 21) for chemical or biological reactions, each of the wells (11; 21) comprising a reaction chamber with at least one opening (111; 211) on a surface (12; 22) of said plate (1; 2), and said array of wells (11; 21) consisting of a plurality of adjacent blocks (13; 23) of wells (11; 21), each block (13; 23) of wells (11; 21) consisting of a plurality of adjacent rows of wells (11; 21), wherein at least one closed space position or void (14; 24) is provided in each block (13; 23) of wells (11; 21) in between said rows of wells (11; 21), said closed space position or void (14; 24) being part of said surface (12; 22) of said plate (1; 2) and lacking a well opening (111; 211).

In this particular embodiment, the openings (111; 211) cover substantially the entire surface (12; 22) of said plate (1; 2) in each block (13; 23) of wells (11; 21) except for said closed space position or void (14; 24). For example, the void (14; 24) is arranged off-center in each respective block (13; 23) of wells (11; 21). The off-center arrangement of said at least one void (14; 24) can include said void (14; 24) in each block (13; 23) being arranged offset in a longitudinal direction and/or in a lateral direction of said plate (1; 2).

Moreover, the closed space position or void (14; 24) in each block (13; 23) of wells (11; 21) is a predetermined area on said surface (12; 22) occupying a similar, preferably identical, area on said surface (12; 22) as is occupied by an opening (111; 211) of each well (11; 21).

In a particular embodiment, the closed space position or void (14; 24) is free of any marker, tag or label, such as a fiducial marker or a marker in the form of an indentation.

The position of the at least one closed space position or void (24) of one block (23) is, in a specific embodiment, different from the position of the at least one closed space position or void (24) of an adjacent block.

Each block (23) can comprise several closed space positions or voids (24), preferably two voids (24), wherein the positions of said voids (24) and/or the distance between said voids (24) vary from one block (23) to another. Moreover, each block (13; 23) can comprise an identical number of wells (11; 21) and/or closed space positions or voids (14; 24).

Still further, each closed space position or void (14; 24) can serve as a reference for spatial encoding of the position of each block (13; 23) on said plate (1, 2).

In yet another embodiment, the at least one closed space position or void (14; 24) is arranged distant to an edge of the respective block (13; 23) of wells (11; 21), and/or wherein said blocks (13; 23) of wells (11; 21) in said plate (1; 2) comprise identical dimensions, each block (13; 23) being suitably sized for a field of view (31; 32) of an imaging device for capturing an image of each block (13; 23).

In each of the embodiments described herein, the cross-sectional area of the opening (111; 211) of each well (11; 21)

is a shape selected from the group of circular, oval and polygonal. In a particular embodiment, the shape is hexagonal.

Moreover, the plate can also include an integrated fluid-distribution system.

Also provided is a method for multiple imaging of a plate as described herein by means of an imaging system, the imaging system comprising:

a holder for said plate (1; 2);

an imaging device for capturing an image of each block (13; 23) of wells (11; 21) of said plate (1; 2) in accordance with its field of view (3);

a processing unit in communication with said imaging device; and a memory unit operably coupled to said processing unit, wherein said holder and/or said imaging device are moveable relatively to each other, and said memory unit includes instructions stored therein for capturing said image of each block (13; 23) of wells (11; 21), wherein the instructions, when executed by said processing unit, cause said processing unit to carry out the following steps:

capturing an image of a first block (13; 23) of wells (11; 21) using said imaging device;

moving said imaging device and/or said plate (1; 2) relatively to each other;

identifying an adjacent block of wells (11; 21) by means of said at least one closed space position or void (14; 24) in the surface (12; 22) of said plate (1; 2) using said imaging device;

moving said holder and/or said imaging device until said adjacent block is in the field of view (3) of the imaging device; and capturing an image of said adjacent block of wells (11; 21) using said imaging device.

In this method, either (a) each step of capturing an image includes (i) identifying the location of each well (11; 21) in said field of view (3) of said imaging device and assigning a global identifier, preferably an index and/or a coordinate, to each well (11; 21) based on a predetermined geometry model of said plate (1; 2) in combination with said at least one closed space position or void (14; 24), (ii) measuring each well (11; 21) in said image, and (iii) storing each measurement result in accordance with the assigned global identifier; or (b) each step of capturing an image includes taking an image and storing said image, and the method further comprises a step of combining the stored images of each block (13; 23) of wells (11; 21) to a combined image of said array of wells (11; 21) by matching said multiple images to each other by means of said closed space position or voids (14; 24), and a step of measuring each well (11; 21) in said combined image and storing each measurement result.

BRIEF DESCRIPTION OF THE FIGURES

Further aspects and advantages of the present disclosure will become apparent from the following description of particular embodiments illustrated in the figures in which.

DETAILED DESCRIPTION

Figure 1:
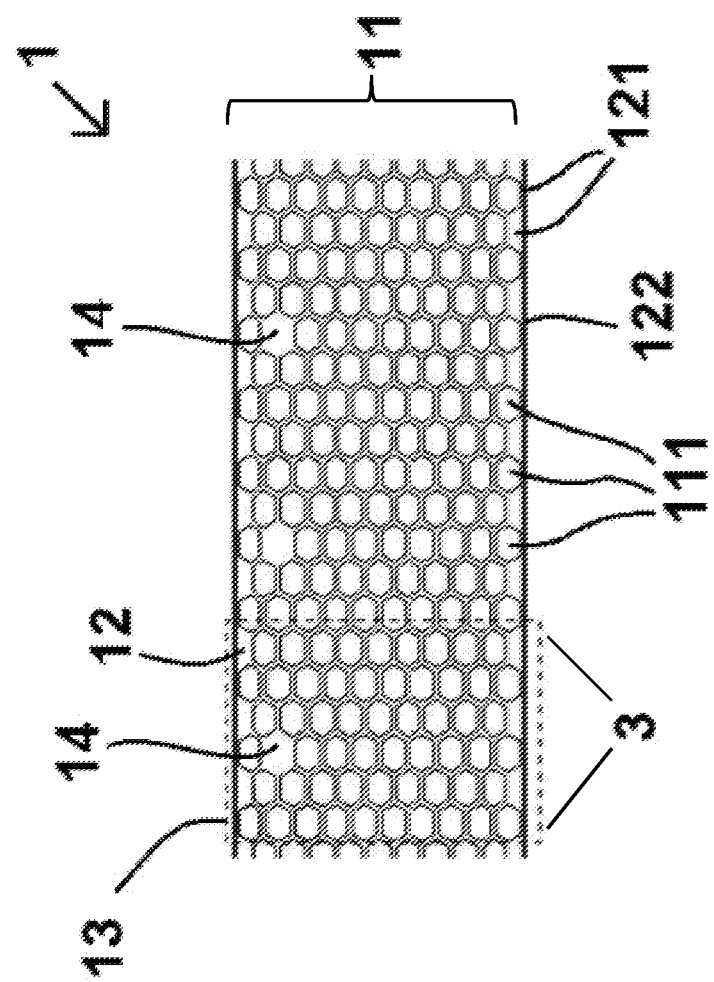
FIG. 1 illustrates a sectional view of a well plate according to a first embodiment of the present disclosure, with an alignment with closed space positions or voids and stage accuracy.

As used herein and in the appended claims, the singular forms "a," "an," and "the" include plural reference unless the context clearly dictates otherwise. Similarly, the words "comprise," "contain" and "encompass" are to be interpreted inclusively rather than exclusively. Similarly, the word "or" is intended to include "and" unless the context clearly indicates otherwise. The terms "plurality," "multiple" or "multitude" refer to two or more.

The present disclosure provides a plate, preferably a multiwell plate, which comprises an array of wells for chemical or biological reactions, such as a real-time PCR or a dPCR. Here, the term "array" (e.g., an "array of wells" or an "array of positions") is used for the entirety of all positions provided in the plate. The plate comprises a top surface including the array of M×N positions, wherein M and N are integers greater than zero, and each position is either a well opening or well defining a reaction chamber for a chemical or biological reaction, or a closed space or void (the terms "well" or "well opening" are used interchangeably herein, and likewise, the terms, "closed space" or "void" are also used interchangeably herein). The array includes a plurality of well openings and at least one closed space or void, and particularly, two or more closed spaces or voids.

Each of the wells comprise a reaction chamber for holding a sample, wherein each well comprises at least one opening provided on a surface of the plate for accessibility of the reaction chamber. Alternatively, each well can also comprise several openings, such as an opening on each surface of the plate.

Furthermore, in accordance with one embodiment of the present disclosure, the array of wells comprises a plurality of adjacent blocks of wells, which blocks could also be referred to as sub-arrays, wherein each block of wells includes a plurality of adjacent rows of wells. In one embodiment, the wells can be arranged in rows, and the rows can be grouped in so-called blocks.

In another embodiment, the array of positions, including well openings and closed spaces or voids, comprises two or more blocks and each block includes a group of positions numbering between one and a number fewer than the total number of positions. In this embodiment, each block includes at least one closed space position, e.g., at least two closed space positions.

The at least two closed space positions can be located in a row that includes a plurality of well openings and the at least two closed spaced positions and the at least two closed space positions can be adjacent to one another in the row or non-adjacent, e.g., separated in the row by at least one well opening. The at least two closed space positions can be located in two or more rows of positions. In this embodiment, the array comprises (i) a first row of positions comprising a first closed space position and two or more well openings, and (ii) a second row of positions comprising a second closed space position and two or more well openings, wherein either the first and second closed space positions are adjacent to one another in the block, or the first and second closed space positions are not adjacent to one another in the block and separated in the block by at least one well opening. The first and second closed space positions can be separated in the block by at least one row of positions.

Still further, the multi-well plate can also include an array boundary and the array further comprises internal and external positions, the external positions being adjacent to the array boundary and the internal positions being removed from the array boundary. In this embodiment, the at least one closed space position occupies an internal position.

In a specific embodiment, the block corresponds to a field of view of an imaging device.

As used herein, neither the rows nor the blocks are to be understood as actual rows or blocks which have a clear separation or boundary distance to the adjacent row or block, but are to be understood as merely virtually existing rows or blocks in a multitude of positions sectored into virtual segments or divisions of positions grouped together in order to be able to monitor only a certain fraction of the array of positions, i.e. a virtual block of positions.

Moreover, in accordance with the plate of the present disclosure, at least one closed space or void, meaning one void or more than one void, is provided in each block of positions, wherein the void is part of the plate's surface. In other words, each block of positions includes respective well openings on the surface of the plate in correlation to a certain segment of the array, and within each block of positions, a certain area of the plate's surface does not exhibit a well opening, i.e., having a closed space or void instead, which can also be referred to as "omitted well opening" or "omitted well," meaning that the surface in this certain area is preferably cavity-less, i.e., untreated or unprocessed. The closed space, void or "omitted well" can also be referred to as a disturbance or defect in the otherwise uniform distribution of well openings across the plate's surface, wherein one void can be provided for each block of positions, or, alternatively, more than one closed space position or void can be provided, wherein a reasonable "waste" of space has to be considered. Also, in accordance with a further configuration, all blocks of positions of the array on the plate can comprise an identical number of well openings and/or voids or closed spaces.

Moreover, the plate can further comprise an integrated fluid-distribution system, which implements a fluidic well plate for transfer of liquids into each well opening, such as a perfused multiwell plate with an array of bioreactors integrated into the multiwell plate format, or the like.

The provision of the at least one closed space position or void position in each block has the advantage that the relative position information of the well openings can be directly encoded in the respective block, wherein each closed to space position or void serves at least as reference for spatial encoding of the position of each block on the plate, without the need of the provision of a respective fiducial marker or the like at the edge of the plate's surface. This provides a block identifying pattern of wells/well openings and voids/closed space positions. Thereby, it becomes possible to stretch the well arrangement or well distribution right up to the edges of the plate, which substantially maximizes available space of the plate's surface for the provision of wells and thus, maximizes the number of wells in the array of wells of the plate. Here, of course, it is to be understood that a certain marginal edge can remain between the plate and the outermost wells due to manufacturing requirements.

Basically, a camera or other kind of imaging device for capturing an image of each block, or actually the human eye, can direct its field of view, or FOV, to a segment of wells and, by identifying a closed space position or void in a certain position, can identify a certain block of wells or positions by means of the particularly positioned closed space position or void in the respective block, i.e. by interpreting the spatial information as provided by the positioning of the closed space position or void. This interpreted information is, then, sufficient to identify each of the wells in each block directly, for example in order to determine the local orientation of the block of wells covered by the FOV, i.e. the shift of the block of wells in x-direction and/or y-direction in an x-y-plane, its rotation, scaling, etc. Further preferably, the blocks of wells in the plate of the present disclosure comprise identical dimensions, in particular in regard to its length and width, such that each block is suitably sized for a FOV of the imaging device to be used for monitoring, measuring and/or simply taking a picture of the respective block of wells.

In accordance with a particular configuration of the plate, the well openings cover substantially the entire surface of the plate in each block except for the closed space position or void. This has the advantage that the entire space provided by the plate can be exploited in a productive and profitable manner, wherein the possibility for orientation in the array of wells can be maintained without the need of space-consuming fiducial markers.

Further, the closed space position or void of each block is arranged off-center within the respective block. Thereby, the information encoded by means of the positioning of the closed space position or void can not only be used to clearly identify the respective block and differentiate the same from other blocks but can also be used for identifying the rotational orientation of the respective block, for example in case the plate has been rotated compared to its usual orientation. Here, for better understanding, it is to be noted that a positioning of each closed space position or void in each block in the same location can also be used for identifying each respective block in that the "rough" identification can be carried out by a detection of the positioning of the FOV of the imaging device itself in relation to the plate, and the "fine" identification of the FOV to be in alignment with the respective block of wells can be carried out by means of the closed space position or void and its target position which can also be in the center of the respective block. However, with an off-center positioning of the closed space position or void, a more simplified way of identifying the monitored block of wells can be achieved. Further, the at least one closed space position or void in each block is arranged offset from the center of the block in a longitudinal direction and/or in a lateral direction of the plate.

Moreover, according to a further configuration of the plate, the position of the at least one void of one block is different from the position of the at least one void of an adjacent block, i.e., the different patterns of positions versus voids in a block constitutes a block identifying pattern of positions that uniquely identifies each block. Also, each block can comprise several closed space positions or voids, such as two voids, wherein the positions of the voids and/or the distance between the voids can vary from one block to another. These features can make it significantly easier to distinguish the blocks from each other. Also, more information can be encoded when implementing these features in the plate, since each further information, such as the number of voids, the distance(s) between two or more voids in one block, and/or the arrangement of the several voids in relation to each other, can be used to correlate with further encoded information. For example, it becomes possible, in case of a predetermined monitoring result in the wells of one block, to encode the information of the result to be monitored by these additional features directly in the respective block. Now, as to the particular arrangement in case of more than one void, such as in the case of the provision of two voids in each block, one void can be positioned in the center, whereas the other void can be positioned offset from the center of the block in a longitudinal direction and/or in a lateral direction of the plate. Alternatively, both voids can be positioned offset from the center of the block in a longitudinal direction and/or in a lateral direction of the plate, wherein the two voids can be separated from each other by one or more well openings in a longitudinal direction and/or in a lateral direction of the plate. Such a particular number and/or arrangement of voids as described above can make it easier, for an imaging device or also for the human eye, to identify the block of wells compared to the other blocks of wells, and might also enhance the practicability of determining the local orientation of the respective block of wells covered by the FOV, i.e. the shift of the block of wells in x-direction and/or y-direction in an x-y-plane, its rotation, scaling, and the like.

In accordance with an additional configuration of the plate of the present disclosure, the closed space position or void in each block can occupy a predetermined area on the surface, which area is similar, or particularly identical, to an area on the plate's surface that is occupied by a well opening. This has the advantage that, during the production of the plate, it is easy to provide the closed space position or void in each block, simply by omitting the provision of a well in one possible position, for each closed space position or void, in each block. Accordingly, the closed space position or void can be identified as "omitted well." Here, even though it is conceivable that each closed space position or void can actually be provided with a kind of marking, for example a printed symbol, letter or number, or a coating with a certain color or shade, during the production of the plate, it is preferred, for the sake of a fast and simple manufacturing process of the usually disposable plate, that the closed space position or void is free of any marker, tag or label, such as a fiducial marker or a marker in the form of an indentation or the like.

Further preferably, the at least one closed space position or void of each block of wells is particularly arranged distant, i.e. with a certain distance, to an edge of the respective block of wells. For example, between each void and the closest edge of the respective block of wells, which is identical to the respective edge of the array of wells and, thus, the respective edge of the plate of the present disclosure, at least one well opening is provided, which then constitutes the distance between the edge and the void. With such a particular positioning of the at least one void on the plate of the present disclosure, a visibility of the void on the surface of the plate in the block of wells, i.e. within the FOV, is improved, which results in a faster and more reliable way of identification of the void. Also, when providing, for example, rows of wells within a block of wells, which rows are shifted or offset to each other, for example by half the dimension/diameter of a well opening, the respective free area between the edge of the plate and the end of a shifted row can not be confused with a void in accordance with the present disclosure.

In a further configuration of the plate of the present disclosure, the cross-sectional area of the opening of each well can have a circular shape, an oval shape, or a polygonal shape, such as a hexagonal shape. With a polygonal shape of the well opening, and particularly with a hexagonal shape of the well opening, it becomes possible to arrange the well openings to each other with less distance in between, i.e. achieve an increased density of distribution of well openings on the plate of the present disclosure. Accordingly, the number of wells in the array of wells of the plate can be further maximized.

According to a further aspect of the present disclosure, a method for multiple imaging of a plate as described above by means of an imaging system is provided. Here, the imaging system comprises a holder for the plate according to the present disclosure, an imaging device for capturing an image of each block of wells of the plate in accordance with its FOV, a processing unit in communication with the imaging device, and a memory unit operably coupled to the processing unit. As examples, the plate can be a multiwell plate with 96 wells, the processing unit can be implemented by a central processing unit CPU, and the memory unit can be implemented by a RAM memory device or a flash memory device connected to the processing unit and the imaging device. Furthermore, the holder and/or the imaging device can be moved relatively to each other, preferably in an automated manner, and the memory unit includes instructions for capturing the image of each block of wells, which instructions are stored in the memory unit beforehand. Here, the movement of the holder and/or the imaging device relatively to each other, which movement is preferably a parallel movement of these components along one direction in certain increments or in a continuous manner, entails a combination of a fixed holder and a moveable imaging device, a moveable holder and a fixed imaging device, or a moveable holder and a moveable imaging device, wherein the last combination is advantageous for achieving an even faster imaging process.

Now, the instructions of the method of the present disclosure, when executed by the processing unit, cause the same to carry out the method step of capturing an image of a first block of wells by means of the imaging device, the method step of moving the imaging device and/or the plate provided on the holder relative to each other, the method step of identifying an adjacent block of wells by means of the at least one void in the surface of the plate using the imaging device, the method step of moving the holder and/or the imaging device until the adjacent block is in the FOV of the imaging device, and the method step of capturing an image of the adjacent block of wells using the imaging device, preferably in this order. With the method as described above, it becomes possible that the imaging device for capturing an image of each block, such as a camera or the like, can direct its FOV to a segment of wells and, by identifying the void provided in the plate, can identify a certain block of wells by means of the particularly positioned void in the respective block, i.e. by interpreting the spatial information as provided by the positioning of the void. Thus, with the interpreted information, the processing unit is able to clearly identify if the FOV aligns with a desired block of wells, or if the imaging device and/or the plate have to be further moved relative to each other, in order for the imaging device to capture the desired image. In the described method, the term "capturing an image" can either be understood as simply taking a picture of the FOV of the imaging device and storing the same in the memory unit without any analysis of the picture, or, alternatively, can be understood as monitoring/observing the FOV of the imaging device and directly analyzing/interpreting the observed details, i.e. the reaction results of the observed wells in the respective block of wells, for example in the form of luminescence measurements results or the like.

Here, the void is also used in order to be able to clearly identify each single well in the respective block of wells as covered by the FOV. Accordingly, in accordance with one configuration of the method, the step of capturing an image can include identifying of the location of each well in the FOV of the imaging device and assigning a so-called global identifier, such as an index and/or a coordinate used for clearly identifying the position of the respective well, to each well based on a predetermined geometry model of the plate in combination with the at least one closed space position or void, and measuring each well in the image. The measurement result/value of each well obtained subsequently well after well is then stored in the memory unit in accordance with the assigned global identifier, in the sense of a measurement value table coinciding with the assigned wells of the plate being filled up well by well. With this configuration, one measurement result is obtained for each well of an image, stored in the measurement value table, and the image is then deleted. Alternatively, as described before, each step of capturing an image can include a simple taking of an image and storing the image in the memory unit, wherein the method then further comprises a step of combining the stored images of each block of wells to a combined image of the array of wells by matching the multiple images to each other by means of the closed space position or voids, which is also referred to as "stitching" in the present technical field, and also a step of measuring each well in the combined image and storing each measurement result. Here, the process of stitching is known in the field of imaging as a process of combining multiple photographic images with overlapping FOVs in order to produce a segmented image, wherein the stitching process is usually performed through the use of particular computer software. Accordingly, the step of measuring each well entails the complete filling up of a measurement value table coinciding with the assigned wells of the plate. Also, with this alternative configuration, overlapped wells and, thus, overlapped measurements results can occur. In order to also only obtain one single measurement result for each well, the thus several measurement results of so the overlapped wells can be averaged to one single mean measurement result. With both the previously described alternatives of the method of the present disclosure, each well can be measured individually, either directly during or subsequently after the imaging of the entire plate, wherein the at least one closed space position or void of the plate improves the identification of each well as well as the alignment of each block of wells with the FOV of the imaging device significantly.

In short, the present disclosure is directed to the use one or multiple voids in the sense of omitted wells in a well plate in order to make it easier to identify each single well, i.e. to assign a certain measurement result to the respective well, along with a maximized use of space for the provision of wells on such a plate, as well as to improve the handling of an imaging system by means of simplifying the orientation between a block of wells to be measured and a FOV of an imaging device of the imaging system.

The present disclosure is not limited to the particular methodology and reagents described herein because they may vary. Although any methods and materials similar or equivalent to those described herein can be used in the practice of the present disclosure, the methods and materials are described herein. Further, the terminology used herein is for the purpose of describing particular embodiments only and is not intended to limit the scope of the present disclosure.

With the plate and the method as described in the present disclosure, it becomes possible to significantly maximize the amount of wells in the plate, since it is possible to encode the position information of the wells directly in the well array, by placing certain areas in the array that do not contain wells, i.e. the above discussed voids, which can also be referred to as "omitted wells." By imaging the well array in bright/dark field illumination, it thus becomes possible to recognize these empty areas, and with image analysis it is possible to measure their size and interpret the thus "encoded information." This interpreted information is sufficient to identify each of the wells directly, and to determine the local orientation of the array on the image, i.e. the x,y-shift, rotation, scaling, etc.

This kind of well location identification system as presented in the present disclosure is particularly important for microwell arrays that need multiple imaging including partial scans and later stitching, or at least a recombination of data. These arrays need to be processed carefully in order not to confuse areas that have been detected serially and also not to double-count overlapping rows and/or forgetting lateral rows of wells. This can be avoided by providing the above mentioned voids, i.e. "omitting" wells in a highly non-regular way, so that each of the partial images comprises its very special own identification mark, or fingerprint, which prevents a user from a confusion of images as well as from a wrong orientation of partial images in regard to each other. Further, the well location identification system eases the identification of possible double rows or cut off rows, i.e. rows of wells that are only partially covered by a single image or single FOV.

In addition, having the structures for orientation within the well array eliminates the need to acquire significantly larger areas than the area of interest, i.e. larger than the actual well array. This renders the imaging process more efficient.

EXAMPLES

The following examples are intended to illustrate various embodiments of the disclosure. As such, the specific modifications as discussed hereinafter are not to be construed as limitations on the scope of the present disclosure. It will be apparent to the person skilled in the art that various equivalents, changes, and modifications may be made without departing from the scope of the present disclosure, and it is thus to be understood that such equivalent embodiments are to be included herein.

In FIG. 1 a sectional view of a well plate 1 according to a first embodiment of the present disclosure is provided, from which a void alignment and stage accuracy can be gathered. In particular, the illustrated area of the well plate 1 of the first embodiment, which is only a part of the entire plate 1, shows a plurality of wells 11 arranged in the form of an array of wells in the plate 1. Here, as illustrated, respective hexagonal openings 111 of the wells 11 are placed in a maximally dense arrangement on a surface 12 of the plate 1, such that only a marginal edge 121 is left between the outermost wells 11 of each row of wells 11 and the actual end 122 of the plate 1. Here, a "row of wells" is only a virtual row of wells 11 and, thus, refers to a single line of wells 11 arranged vertically, i.e. from top to bottom in FIG. 1, wherein a "long" row of wells 11 counts ten wells 11, and every other row, or "short" row, counts nine wells 11, an arrangement that is due to the hexagonal cross-section of the openings 111 of each well 11 in combination with the desired maximally dense arrangement of wells 11 in the plate 1. Thereby, each "short" row of wells 11 provides a somewhat larger edge 121 between the outermost well 11 in this row and the actual end 122 of the plate 1, which, however, does not change the fact that the omitting of fiducial markers as is possible with the present disclosure still enables to use the space as provided by the surface 12 of the plate 1 in a highly efficient manner. Further, as mentioned above, a plurality of rows of wells 11 constitutes a block 13 of wells, which is of course only a virtual block 13 without any visible margins as already explained above. Here, in the first embodiment, the block of wells 13 as illustrated in FIG. 1 counts six rows of wells 11. A field of view 3 of an imaging device (not shown) basically coincides with the block 13 of wells 11, and also covers an insignificant part of an adjacent row of wells 11 at the edge of the block 13, in order to be able to comprehensively cover the six rows of wells 11 of the block 13 of wells 11.

Now, as global identifier (see explained above), one void 14 is provided in the block 13 of wells 11 monitored by the field of view 3. As can be seen in the adjacent shown blocks of wells 11, further voids 14 are provided, wherein all voids 14 of all blocks 13 of wells 11 of the plate 1 are used to differentiate the different blocks 13 from each other. Even though the voids 14 are always provided in the same off-center position in each block 13, a "rough" identification can be carried out by a detection of the positioning of the field of view 3 in relation to the plate 1, i.e. the vague determination of the positioning of the plate 1, or of its (not shown) holder and the imaging device in relation to each other, in order to establish an approximate orientation and, thus, identification of wells. Then, by means of the void 14, a "fine" identification of the field of view 3 and its content is possible, for example, a well positioned vertically above the void 14 can be assigned as "one above the void", the wells below the void 14 can be assigned as "one below the void", "two below the void", etc. Accordingly, in the field of view 3, each well 11 can be identified in relation to the void 14, and adjacent blocks 13 of wells 11 can also be identified in relation to each other by means of the voids 14, since only one single void 14 is to be aligned with a certain position in the field of view 3 when capturing an image by means of the imaging device.

Figure 2A:
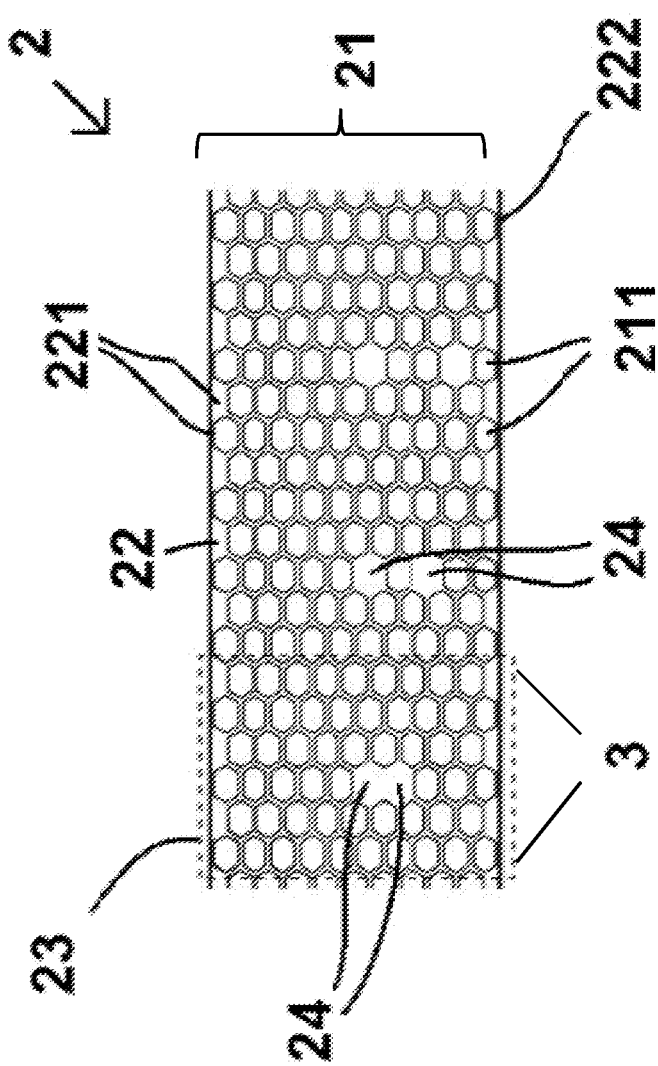
FIG. 2A illustrates a sectional view of a well plate according to a second embodiment of the present disclosure, with an alignment with unique patterns of closed space positions or voids.

In FIG. 2A a sectional view of a well plate 2 according to a second embodiment of the present disclosure is provided, in which a unique pattern of voids is shown. In particular, the illustrated area of the well plate 2 of the second embodiment, which is only a part of the entire plate 2, shows a plurality of wells 21 arranged in the form of an array of wells in the plate 2. Here, similar to the first embodiment shown in FIG. 1, hexagonal openings 211 of the wells 21 are placed in a maximally dense arrangement on a surface 22 of the plate 2, such that a similar marginal edge 221 is left between the outermost wells 21 of each row of wells 21 and the actual end 222 of the plate 2. Further similarly, a plurality of the virtual rows of wells 21 of the plate 2 again constitutes a virtual block 23 of wells, wherein the block of wells 23 as illustrated in FIG. 2 counts six rows of wells 21. The field of view 3 of the imaging device, which is identical to the one from the first embodiment, basically coincides with the block 23 of wells 21, and also covers an insignificant part of an adjacent row of wells 21 at the edge of the block 23, in order to be able to comprehensively cover the six rows of wells 21 of the block 23 of wells 21.

Now, as global identifier, a combination of two adjacent voids 24 is provided in the block 23 as monitored by the field of view 3. As can be seen in the adjacent shown blocks of wells 21, further combinations of two voids 24 are provided, wherein the different combinations of voids 24 differ from each other in that the voids 24 comprise different distances in between the two voids 24. In FIG. 2, besides the combination of two directly adjacent voids 24 in the block 23 as monitored by the field of view 3, another block with a combination of two voids 24 with one opening 211 in between is shown, and another combination of two voids 24 with two openings 211 in between is shown. Here, even though the distance between the voids 24 is enlarged only in the vertical direction of the illustration, which direction coincides with a lateral direction of the plate 2, the distance between the voids 24 can also be provided in a horizontal direction in the illustration, which direction coincides with a longitudinal direction of the plate 2. Here again, all combinations of voids 24 in the virtual blocks of the plate 2 are used to differentiate the different blocks 23 from each other. Even though the combinations of voids 24 are always provided in the same off-center position in each block 23, a "rough" identification and a "fine" identification can be carried out as explained with reference to the first embodiment. Accordingly, in the field of view 3, each well 21 can be identified in relation to the respective combination of voids 24, and adjacent blocks 23 of wells 21 can also be identified in relation to each other by means of the differing combinations of voids 24. In the second embodiment, the positions of the voids 24 and/or the distance between the voids 24 of the combination of voids 24 can vary from one block to another, which enhances the distinguishability between the different blocks significantly. Also, more information can be encoded with the use of a combination of voids 24, such as the local orientation of the respective block of wells covered by the field of view 3, i.e. the shift of the block 23 of wells 21 in x-direction and/or y-direction in an x-y-plane of the plate 2, its rotation, scaling, and the like.

Figure 2B:
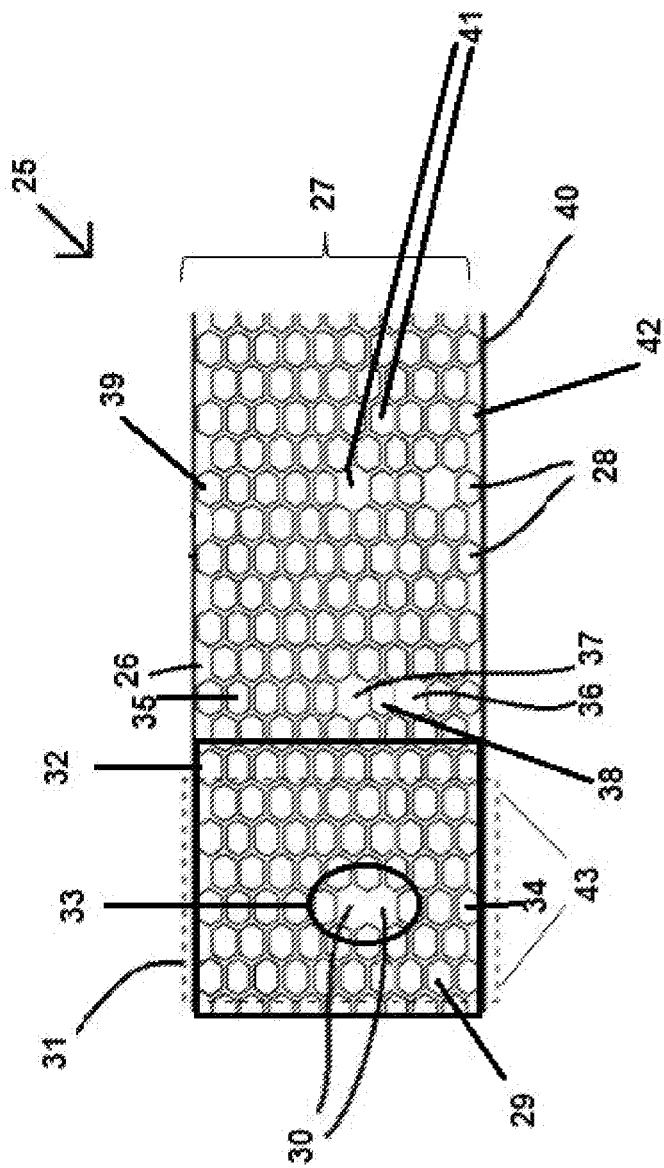
FIG. 2B illustrates an additional sectional view of a well plate according to a second embodiment of the present disclosure, with an alignment with unique patterns of closed space position or voids.
Figure 3:
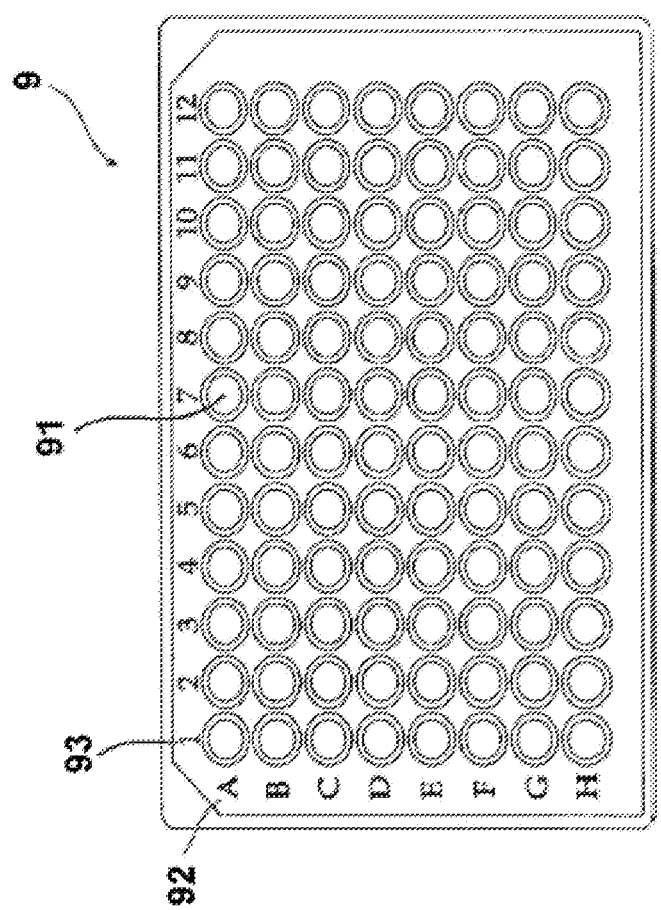
FIG. 3 illustrates a top view of a multiwell plate according to prior art.
Figure 4:
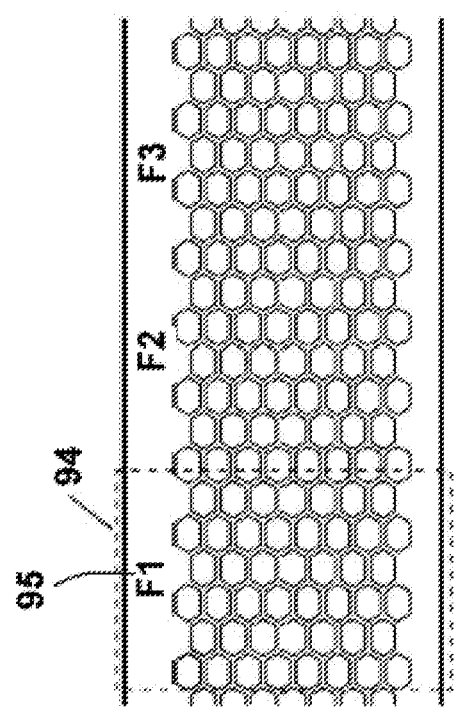
FIG. 4 illustrates a sectional view of a well plate according to further prior art.

FIG. 2B shows yet another illustration of the second embodiment of the disclosure. The multi-well plate 25 has a top surface 26 including an array 27 of M×N positions 28. Each position is selected from (i) a well opening 29 defining a reaction chamber for a chemical or biological reaction, or (ii) a closed space 30, wherein the array comprises two or more blocks 31, each block comprising a group of positions 32 numbering between one and a number fewer than the total number of positions in the array, and each block comprises a block-identifying pattern of positions including at least one closed space position 33. Here, similar to the embodiment shown in FIG. 2A, hexagonal openings of the well openings are placed in a maximally dense arrangement on a surface of the plate, such that a similar marginal edge is left between the outermost wells of each row of wells and the actual end of the plate. In FIG. 2B, the block-identifying pattern of positions includes at least two closed space positions (both identified as position 30 in pattern 33), The at least two closed space positions 30 are located in a row of positions 34 comprising a plurality of well openings and the at least two closed space positions. In the embodiment shown in row 34, the at least two closed space positions are adjacent to one another in the row. An alternative embodiment is shown in row 35 in which the at least two closed space positions 36 and 37 are not adjacent to one another and separated in the row by at least one well opening 38. In yet another embodiment, the at least two closed space positions can be separated in the row by at least two well openings (shown in row 39). The at least two closed space positions can be located in two or more rows of positions (not shown). Moreover, the multi-well plate 25 further comprises an array boundary 40 and the array further comprises internal 41 and external 42 positions, the external positions being adjacent to the array boundary and the internal positions being removed from the array boundary. In a particular embodiment, the at least one closed space position occupies an internal position 41. Finally, the block corresponds to a field of view 43 of an imaging device (not shown).

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A multi-well plate comprising a top surface including an array of M×N positions, wherein M and N are integers >0 and each position is selected from (i) a well opening defining a reaction chamber for a chemical or biological reaction, or (ii) a closed space that is a part of the top surface of the multi-well plate and free of any marker, tag, or label, wherein the array comprises two or more blocks, each block comprising a group of positions numbering between one and a number fewer than the total number of positions in the array, and each block comprises a block-identifying pattern of positions including at least two closed space positions, wherein a distance between the at least two closed space positions is varied from one block to another such that each block-identifying pattern is distinguishable from one another.

2. The multi-well plate of claim 1 wherein the at least two closed space positions are located in a row of positions comprising a plurality of well openings and the at least two closed space positions.

3. The multi-well plate of claim 1 wherein the at least two closed space positions are located in two or more rows of positions.

4. The multi-well plate of claim 3 wherein each of the at least two closed space positions occupies an internal position.

5. The multi-well plate of claim 3 wherein the array comprises (i) a first row of positions comprising a first closed space position and two or more well openings, and (ii) a second row of positions comprising a second closed space position and two or more well openings.

6. The multi-well plate of claim 5 wherein the first and second closed space positions are not adjacent to one another in the block and separated in the block by at least one well opening.

7. The multi-well plate of claim 6 wherein the first and second closed space positions are separated in the block by at least one row of positions.

8. The multi-well plate of claim 1 wherein the multi-well plate further comprises an array boundary and the array further comprises internal and external positions, the external positions being adjacent to the array boundary and the internal positions being removed from the array boundary.

9. The multi-well plate of claim 1 wherein the block corresponds to a field of view of an imaging device.

10. The plate of claim 1, wherein the cross-sectional area of said opening of each well is a shape selected from a circle, oval, or polygon.

11. The plate of claim 10, wherein the shape is a hexagon.

12. A plate comprising an array of wells for chemical or biological reactions, each of the wells comprising a reaction chamber with at least one opening on a surface of said plate, and said array of wells consisting of a plurality of adjacent blocks of wells, each block of wells consisting of a plurality of adjacent rows of wells, wherein at least two voids are provided in each block of wells in between said rows of wells, said at least two voids being part of said surface of said plate and lacking a well opening, wherein said at least two voids are free of any marker, tag, or label, and wherein a distance between the at least two voids is varied between adjacent blocks to form a block-identifying pattern.

13. The plate of claim 12, wherein said at least two voids are arranged off-center in each respective block of wells.

14. The plate of claim 12, wherein each void serves as a reference for spatial encoding of the position of each block on said plate.

15. The plate of claim 12, wherein each of said at least two voids is arranged distant to an edge of the respective block of wells, and/or wherein said blocks of wells in said plate comprise identical dimensions, each block being sized to correspond to a field of view of an imaging device for capturing an image of each block.

16. A method for multiple imaging of a plate of claim 12 using an imaging system, the imaging system comprising:
 a holder for said plate;
 an imaging device for capturing an image of each block of wells of said plate in accordance with its field of view;
 a processing unit in communication with said imaging device; and
 a memory unit operably coupled to said processing unit, wherein
 said holder and/or said imaging device are moveable relatively to each other, and
 said memory unit includes instructions stored therein for capturing said image of each block of wells,
 wherein the instructions, when executed by said processing unit, cause said processing unit to carry out the following steps:
  capturing an image of a first block of wells using said imaging device;
  moving said imaging device and/or said plate relative to each other;
  identifying an adjacent block of wells by means of said at least one void in the surface of said plate using said imaging device;
  moving said holder and/or said imaging device until said adjacent block is in the field of view of the imaging device; and
  capturing an image of said adjacent block of wells using said imaging device.

* * * * *